(12) United States Patent
Nagarajan et al.

(10) Patent No.: US 11,219,365 B2
(45) Date of Patent: Jan. 11, 2022

(54) OPHTHALMOLOGIC IMAGING APPARATUS

(71) Applicant: REMIDIO INNOVATIVE SOLUTIONS PVT. LTD., Bengaluru (IN)

(72) Inventors: Shanmuganathan Nagarajan, Thirvarur-Dt (IN); Anand Sivaraman, Bangalore (IN)

(73) Assignee: REMIDIO INNOVATIVE SOLUTIONS PVT. LTD., Bengaluru (IN)

( * ) Notice: Subject to any disclaimer, the term of this patent is extended or adjusted under 35 U.S.C. 154(b) by 380 days.

(21) Appl. No.: 16/078,338

(22) PCT Filed: Sep. 4, 2017

(86) PCT No.: PCT/IN2017/050380
§ 371 (c)(1),
(2) Date: Aug. 21, 2018

(87) PCT Pub. No.: WO2018/047198
PCT Pub. Date: Mar. 15, 2018

(65) Prior Publication Data
US 2019/0021591 A1 Jan. 24, 2019

(30) Foreign Application Priority Data
Sep. 7, 2016 (IN) .............................. 201641030623

(51) Int. Cl.
*A61B 3/14* (2006.01)
*A61B 3/12* (2006.01)
*A61B 3/00* (2006.01)

(52) U.S. Cl.
CPC .............. *A61B 3/14* (2013.01); *A61B 3/0008* (2013.01); *A61B 3/12* (2013.01); *A61B 3/0025* (2013.01)

(58) Field of Classification Search
CPC ........... A61B 3/0008; A61B 3/12; A61B 3/13; A61B 3/132; A61B 3/135; A61B 3/14
(Continued)

(56) References Cited

U.S. PATENT DOCUMENTS 4,253,743 A * 3/1981 Matsumura ............ A61B 3/103
351/206
5,255,026 A * 10/1993 Arai ......................... A61B 3/14
351/206

(Continued)

OTHER PUBLICATIONS

International Patent Application No. PCT/IN2017/050380, International Search Report dated Mar. 6, 2018.

(Continued)

*Primary Examiner* — Nicholas R. Pasko
(74) *Attorney, Agent, or Firm* — Leber IP Law; Celia H. Leber

(57) ABSTRACT

The present subject matter relates to an ophthalmologic imaging apparatus, which can capture reflex-free retinal images of a subject's eye. The imaging apparatus comprises light sources arranged on an illumination axis. A first shield placed at a distance from a first condenser lens, which is placed in front of a photographic light source on the illumination axis. The first shield has a central opaque portion on which an observation light source is mounted, and an outer pair of coaxial annular transparent regions. A diffuser is placed in front of the observation light source. A second shield has a central opening portion and mounted on the diffuser. The imaging apparatus further comprises a porosity mirror mounted on a porosity tube.

14 Claims, 4 Drawing Sheets

(58) Field of Classification Search
USPC .................................. 351/206, 207, 210, 221
See application file for complete search history.

(56) References Cited

U.S. PATENT DOCUMENTS

| | | | | |
|---|---|---|---|---|
| 5,742,374 | A * | 4/1998 | Nanjo | A61B 3/145 351/206 |
| 7,572,009 | B2 * | 8/2009 | Suzuki | A61B 3/12 351/201 |
| 7,677,730 | B2 * | 3/2010 | Shimizu | A61B 3/14 351/206 |
| 8,480,232 | B2 * | 7/2013 | Aikawa | A61B 3/14 351/206 |
| 8,506,081 | B2 * | 8/2013 | Matsumoto | A61B 3/12 351/214 |
| 9,398,851 | B2 | 7/2016 | Anand et al. | |
| 9,474,443 | B2 | 10/2016 | Yoshino | |
| 2008/0002152 | A1 | 1/2008 | Collins et al. | |
| 2011/0051086 | A1 * | 3/2011 | Takai | A61B 3/12 351/206 |
| 2011/0051090 | A1 * | 3/2011 | Takai | A61B 3/12 351/208 |
| 2013/0027666 | A1 * | 1/2013 | Aikawa | A61B 3/14 351/214 |
| 2013/0182217 | A1 * | 7/2013 | Cheng | A61B 3/14 351/206 |
| 2013/0208242 | A1 * | 8/2013 | Itoh | A61B 3/14 351/208 |
| 2013/0250242 | A1 | 9/2013 | Cheng et al. | |
| 2013/0321906 | A1 * | 12/2013 | Kriofske | G02B 21/0016 359/363 |
| 2014/0146288 | A1 * | 5/2014 | Anand | A61B 3/0008 351/207 |
| 2015/0374232 | A1 * | 12/2015 | Yoshino | A61B 3/12 351/206 |

OTHER PUBLICATIONS

International Patent Application No. PCT/IN2017/050380, Written Opinion dated Mar. 6, 2018.

* cited by examiner

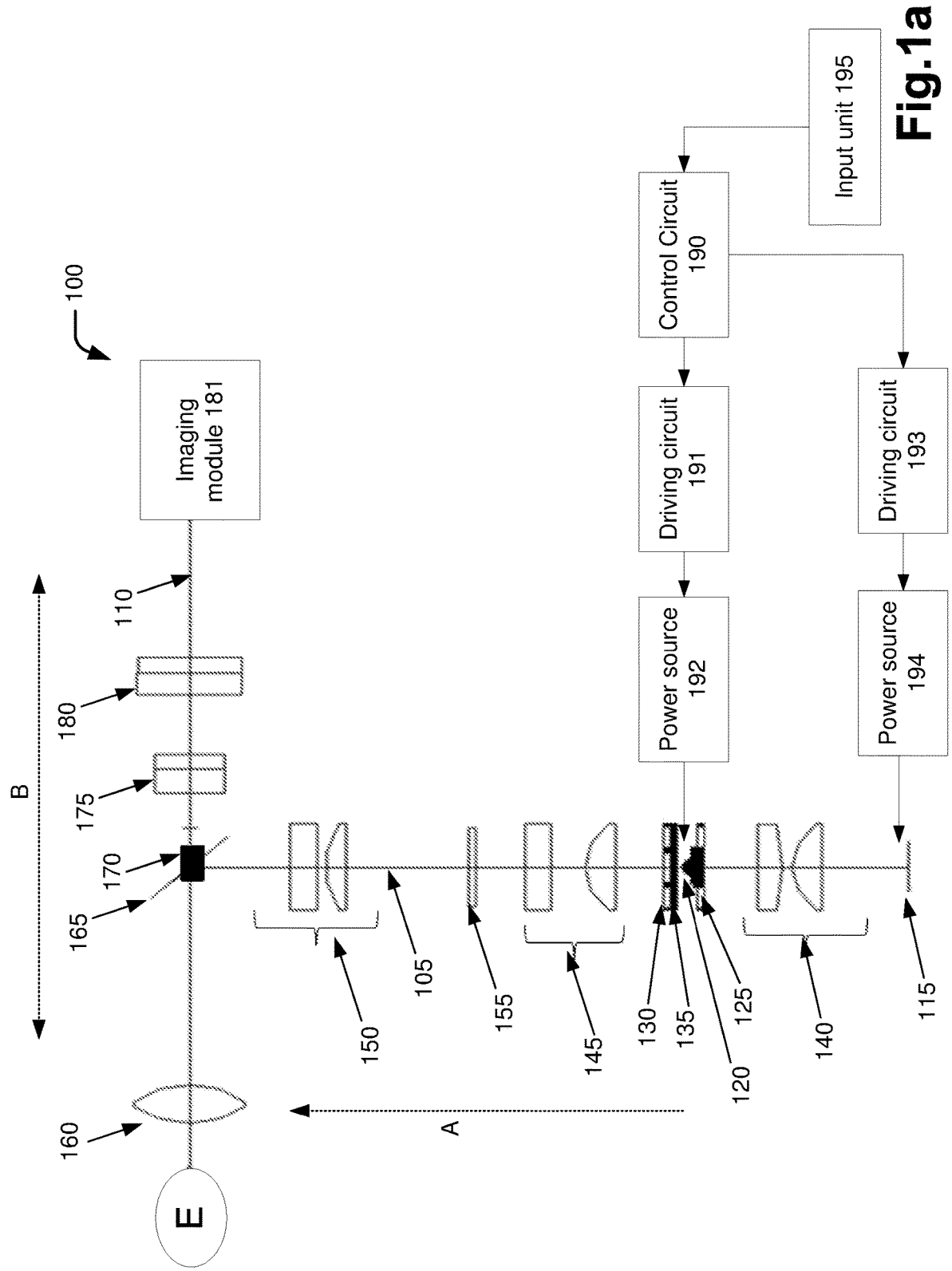

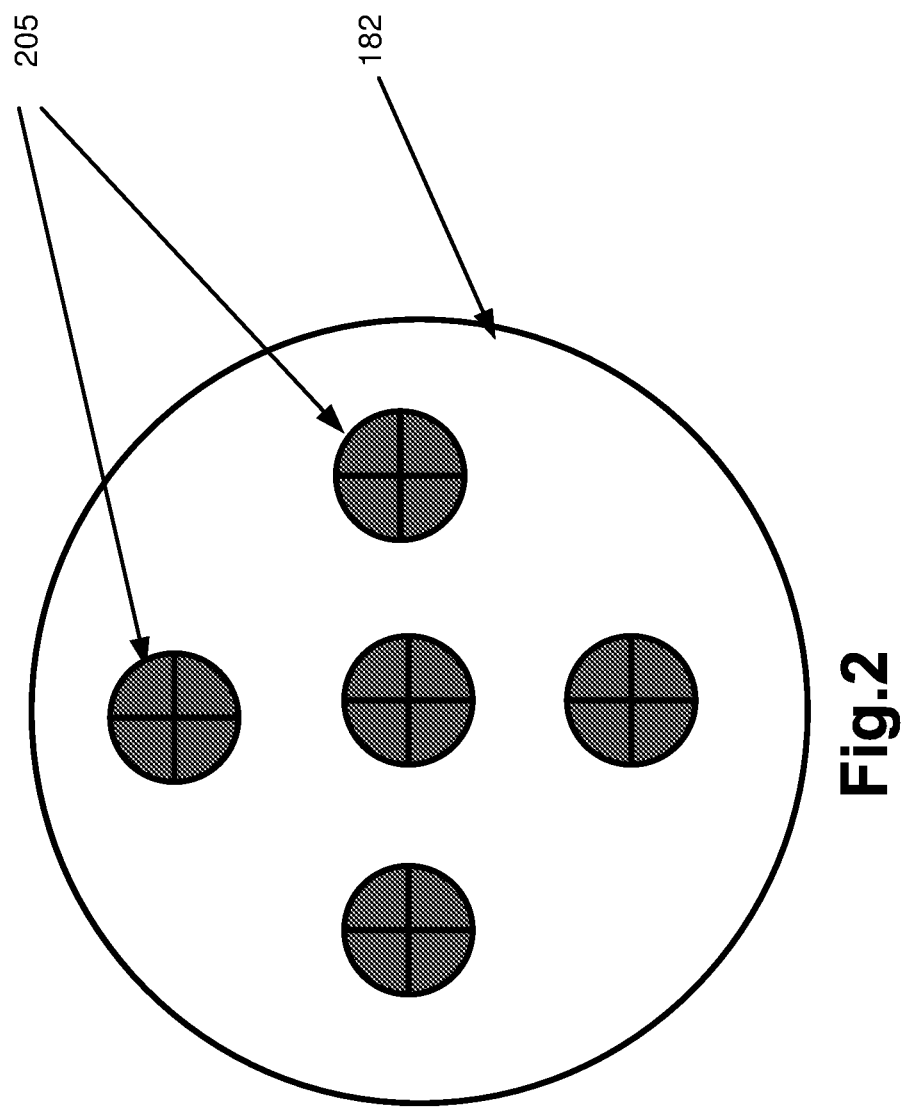

OPHTHALMOLOGIC IMAGING APPARATUS

CROSS REFERENCE TO RELATED APPLICATIONS

This application is a national phase entry of International Patent Application No. PCT/IN2017/050380, filed Sep. 4, 2017, which claims the benefit under 35 U.S.C. § 119(b) to Indian Patent Application No. 201641030623, filed Sep. 7, 2016, the entire contents of which are hereby incorporated by reference.

TECHNICAL FIELD

The subject matter described herein relates, in general, to an imaging apparatus, and, in particular, to an ophthalmologic imaging apparatus, which can capture retinal images.

BACKGROUND

Ophthalmoscopy is a test that allows a clinician to see inside the fundus of the eye and other structures using an ophthalmoscope or funduscope. It is done as part of an eye examination and crucial in determining the health of the retina and the vitreous humor. A direct ophthalmoscope produces an upright, or unreversed, image of approximately 15 times magnification. An indirect ophthalmoscope produces an inverted, or reversed, direct image of 2 to 5 times magnification and allows for wider view of the inside of the eye that is useful in detecting several eye related diseases like glaucoma, diabetic retinopathy or eye related imperfections like retinal detachment etc.

BRIEF DESCRIPTION OF THE DRAWINGS

The detailed description is provided with reference to the accompanying figures. In the figures, the left-most digit(s) of a reference number identifies the figure in which the reference number first appears. The same numbers are used throughout the drawings to reference like features and components.

FIG. 1a is a diagrammatic view of an ophthalmologic imaging apparatus, in accordance with an embodiment of the present subject matter.

FIG. 2 shows an arrangement of LEDs on the first shield of the FIG. 1a, in accordance with an embodiment of the present subject matter.

DETAILED DESCRIPTION

Figure 1B:
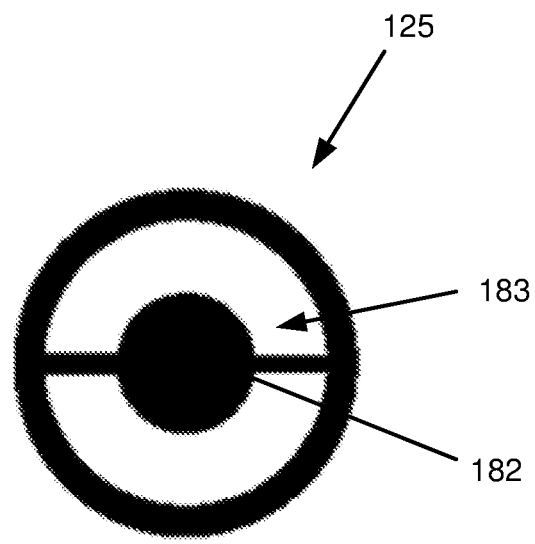
FIG. 1b shows a structure of a first shield used in the ophthalmologic imaging apparatus of the FIG. 1a, in accordance with an embodiment of the present subject matter.

The subject matter described herein relates to an ophthalmologic imaging apparatus, which can capture reflex-free retinal images. In an embodiment, the ophthalmologic imaging apparatus is adapted to capture reflex-free retinal images in different modes, for example, mydriatic, non-mydriatic, red free Fundus Fluorescein Angiography (FFA), Indocyanine Green (ICG) Angiography, etc.

Retinal images or fundus images have been broadly used for diagnosis of various diseases of human retina. Generally, artificially induced enlargement of a pupil of a subject's eye is necessary in order to allow sufficient light into the subject's eye for fundus observation and image capture. In mydriatic fundus photography, subject's eye is subjected to dilation before examination or observation by using a mydriatic agent. On the other hand, non-mydriatic fundus photography, in which the subject's eye does not require prior pharmacologic dilation, is commonly used in photography and relies on infrared wavelength light by which the subject's eye does not feel glare during the observation or the examination. A non-mydriatic fundus camera has been conventionally used for fundus examination and image capture without dilation of the subject's eye. With such a conventional fundus camera, the fundus of the subject's eye is illuminated with the infrared light for observation, and the image of the fundus is captured using a different light source for example, visible light source.

It is well known that when an eye to be observed or examined is illuminated with an illumination light beam, a part of the illumination light beam is reflected on the surface of cornea and the lens or diffused in them. Reflected light from surface of the cornea results in reflection appearing in the fundus image.

Further, in some conventional retinal imaging devices, an illumination light source for observing or examining the subject's eye, and a photographic light source for imaging are arranged on different optical axes, which make such retinal imaging devices bulky, difficult to use and complicated in design. In some other conventional retinal imaging devices, the illumination light source and the photographic light source are arranged on a same optic axis; however, such retinal imaging devices use a long illumination track length.

In order to prevent corneal reflections as well as pupil reflections, some of the conventional fundus imaging apparatus uses a ring shaped aperture. The ring shaped aperture is provided to limit the light passing to an image plane so that the illumination light reflected at the cornea does not overlap at the image plane with the light, which has been reflected at the fundus and passed through the objective lens to the image plane.

The present subject matter relates to an ophthalmologic imaging apparatus, which can capture reflex-free retinal images with the help of at least a first shield, a second shield, a porosity mirror and a porosity tube. In an embodiment, the first shield and the second shield are designed in such a way that the reflex-free retinal images may be captured.

FIG. 1a is a diagrammatic view of an ophthalmologic imaging apparatus 100, in accordance with an embodiment of the present subject matter. The ophthalmologic imaging apparatus 100 of the present subject matter is capable of operating in different modes such as a live view mode and a photographic mode. The live view mode of the ophthalmologic imaging apparatus 100 may be used at the time of observation or examination of subject's eye E, and the photographic mode of the imaging apparatus 100 may be used at the time of imaging retina of the subject's eye E. The FIG. 1a shows the diagrammatic view of the ophthalmologic imaging apparatus 100 comprising different optical components placed along an illumination axis 105, and an imaging axis 110, which is substantially perpendicular to the illumination axis 105. Hereinafter, the terms retina and fundus may be used interchangeably. Further, the ophthalmologic imaging apparatus 100 may be hereinafter referred to as an imaging apparatus 100.

In an embodiment, the imaging apparatus 100 comprises at least one of a photographic light source 115 and an observation light source 120. For example, the photographic light source 115 is one of a flash tube, a tungsten filament bulb, halogen bulb, xenon flash lamp or LED sources, and the observation light source 120 comprises plurality of LEDs operating at different predefined wavelengths of light, and a halogen light lamp. Arrangement and the operation of the plurality of LEDs are explained in detail with respect to FIG. 2 and FIG. 3.

In an embodiment, the imaging apparatus 100 comprises the photographic light source 115 for photographing the subject's eye E and an observation light source 120 for observing the subject's eye E. In an aspect, the imaging and observation of the eye E is performed along the illumination axis 105 using either the photographic light source 115 or the observation light source 120.

In another embodiment, the imaging apparatus 100 comprises the observation light source 120 for observing the subject's eye E and for photographing the subject's eye E.

The observation light source 120 is placed at a spaced apart distance from the photographic light source 115 along the illumination axis 105, as shown in the FIG. 1a. In an embodiment, the position of the observation light source 120 and the photographic light source 115 may be interchangeable.

The imaging apparatus 100 further comprises at least a first shield 125, a second shield 130, a diffuser 135, a first condenser lens 140, a second condenser lens 145, at least one projection lens 150, and a transparent plate 155 placed along the illumination axis 105. In an embodiment, the first shield 125 and the second shield 130 are ring shaped.

The imaging apparatus 100 further comprises an objective lens 160, a porosity mirror 165, a porosity tube 170, a collimating lens 175, a converging lens 180, and an imaging module 181 placed along the imaging axis 110. In an example, the imaging module 181 may be a camera lens of a smart phone. In another example, the imaging module 181 is a lens for a direct view by a human eye. The imaging module 181 may be monocular or binocular. The objective lens 160 is placed to face the eye E to be examined.

The first shield 125 is placed at a distance from the first condenser lens 140. The first condenser lens 140 is placed in front of the photographic light source 115 on the illumination axis 105 for condensing incident beam and emanating a condensed incident beam. In an embodiment, the first shield 125 serves to prevent corneal reflections during the photographic mode.

In an embodiment, the first shield 125 has a central opaque portion 182 on which the observation light source 120 is mounted and an outer pair of coaxial annular transparent portion 183, as shown in the FIG. 1b. In an embodiment, the observation light source 120 is mounted at center on the central opaque portion 182 of the first shield 125 along the illumination axis 105. In another embodiment, the observation light source 120 is mounted between the center and periphery of the central opaque portion 182 of the first shield 125. For instance, the observation light source 120 is mounted very close to the center of the central opaque portion 182 of the first shield 125. Thus, the present subject matter reduces loss of light by mounting the observation light source 120 either at the center or between the center and periphery of the central opaque portion 182 of the first shield 125, rather than mounting the observation light source 120 around the circumference of the first shield 125 as disclosed in conventional arts.

In an embodiment, the diffuser 135 is placed in front of the observation light source 120 to diffuse an illumination light beam emitted from the observation light source 120. The diffuser 135 is adapted to receive the illumination light beam emitted from at least one LED of the plurality of the LEDs of the observation light source 120 mounted on the first shield 125. The diffuser 135 can be constructed from glass, plastic, or any other substrate that will allow for near-uniform illumination.

Figure 1C:
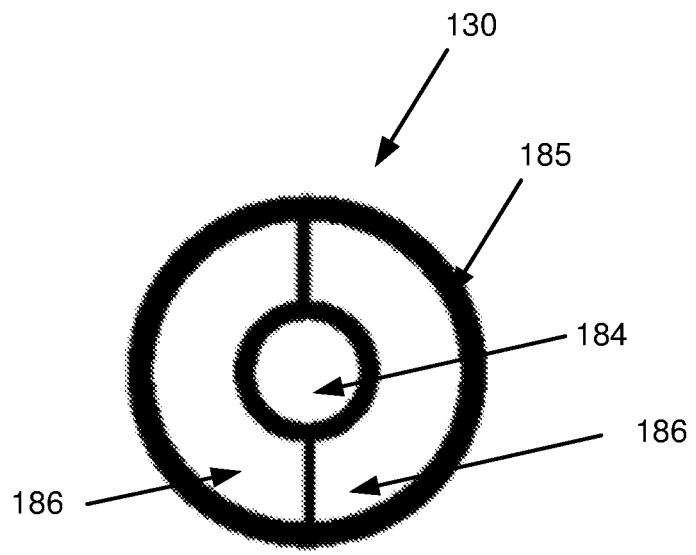
FIG. 1c shows a structure of a second shield used in the ophthalmologic imaging apparatus of the FIG. 1a in accordance with an embodiment of the present subject matter.

The second shield 130 is mounted on the diffuser 135. The second shield 130 has a central opening portion 184, an outer pair of coaxial annular opaque portion 185 and a donut shaped portion 186, as shown in FIG. 1c. The second shield 130 creates an annular illumination pattern from the illumination light beam. In an example, the annular illumination pattern is of a donut shaped illumination pattern or in the form of annulus having a region bounded by two concentric circles. In an embodiment, when the photographic light source 115 is switched ON, the image of the annular illumination pattern is formed at the corneal plane, since the central portion of the illumination light beam is blocked by the central portion 182 of the first shield 125 and subsequently unblocked illumination light beam passes through the donut shaped portion 186 of the second shield 130 to create the annular illumination portion.

As previously discussed, the imaging apparatus 100 comprises the transparent plate 155 having a black dot absorber, and the transparent plate 155 is placed at a distance from the second shield 130. For example, the transparent plate 155 is a glass plate, and the light absorber is a black dot placed in the center of the glass plate. In an aspect, the black dot may prevent the objective lens 160 reflection. Further, the imaging apparatus 100 comprises the second condenser lens 145 placed between the transparent plate 155 and the second shield 130. The second condenser lens 145 is corrected for spherical and chromatic aberrations, as would be appreciated by those skilled in the art.

Furthermore, the imaging apparatus 100 comprises at least one projection lens 150 placed between the porosity tube 170 and the transparent plate 155.

The porosity mirror 165 is mounted on the porosity tube 170. The porosity mirror 165 is mounted at an angle with respect to the imaging axis 110, and the porosity tube 170 is disposed substantially perpendicular to the illumination axis 105. Further, at least a portion of the porosity tube 170 protrudes out from a reflecting face of the porosity mirror 165, thus forming an elliptical stopper. In an aspect, the porosity mirror 165 is located in conjugate with the pupil of the subject's eye E with respect to objective lens 160, i.e., donut shaped illumination at the porosity mirror 165 and the porosity tube 170 is formed by the objective lens 160 at pupil plane of the subject's eye E. This results in preventing pupil reflections.

Further, the collimating lens 175 and the converging lens 180 are placed in series along the imaging axis 110, and placed between the porosity tube 170 and the imaging module 181. For example, a physician may directly view through the imaging module 181 and observe the images of the eye E under test.

In an embodiment, the imaging apparatus 100 further comprises a control circuit 190. Outputs of the control circuit 190 may be connected to driving circuits 191 and 193, respectively. The driving circuits 191 and 193 may control the supply of power to the observation light source 120 and the photographic light source 115 using power sources 192 and 194, respectively. For example, the driving circuits 191 and 193 include one or more electronic components such as transistors. The imaging apparatus 100 further includes an input unit 195 through, which an operator can provide input commands. For instance, the input unit 195 may include one or more actuate buttons provided on a body of the imaging apparatus 100. Upon receiving an input command from an operator, the control circuit 190 may send an operation signal to one or both of the driving circuits 191, 193 based on the input. For instance, if an operator inputs to operate the imaging apparatus 100 in the photographic mode, then the control circuit 190 sends an operational signal to the driving circuit 193, which is connected to the photographic light source 115. Likewise, if an operator inputs to operate the imaging apparatus 100 in the live view mode, then the control circuit 190 sends an operational signal to the driving circuit 191, which is connected to the observation light source 120. In an embodiment, the control circuit 190 may control the intensity of the light emitted by the one or more LEDs, which are in ON condition. In another embodiment, the operation of the plurality of LEDs of the observation light source 120 may be controlled by a mobile phone, through Bluetooth or Wi-Fi.

In operation, when an operator provides an input to operate the imaging apparatus 100 in the observation mode or in the live view mode, the driving circuit 191 sends an operational signal to switch ON the power source 192 connected to the observation light source 120. When the observation light source 120 is switched ON, the diffuser 135 receives the illumination light beam emitted from at least one LED of the plurality of LEDs of the observation light source 120. In an example, the diffuser 135 receives the illumination light beam emitted from an infrared LED operating at a wavelength of about greater than 700 nm to operate the imaging apparatus 100 in a non-mydriatic mode. The second shield 130 mounted on the diffuser 135 in the path of the illuminating light beam, converts the illumination light beam to the annular illumination pattern. The annular illumination pattern is focused at the porosity mirror 165 through the second condenser lens 145, the transparent plate 155, the at least one projection lens 150, and then directed through the objective lens 160 to the subject's eye E. The image of the annular illumination pattern is chosen to be in focus at the surface of the cornea and of dimensions that allow the illumination light to pass through the pupil into vitreous humour to illuminate the retina. In an embodiment, the second shield 130 and the porosity tube 170 serves to prevent the reflections from the cornea while observing or examining the eye E during the live view mode of the imaging apparatus 100, and also while capturing the image of the fundus during the photographic mode of the imaging apparatus 100. In an embodiment, the observation light source 120 it self can be used for observing the fundus and capturing fundus photograph in different imaging modes viz. color, ICG, red free, IR imaging.

Further, in an embodiment, when the photographic light source 115 is actuated to photograph the illuminated portion of the retina, the reflected light from the retina is directed to the porosity mirror 170 through the objective lens 160. The porosity mirror 170 is designed and positioned in such a way that the reflected rays are transmitted along the imaging axis 110 to the imaging module 181 through the collimating lens 175 and converging lens 180. Thus, the image of the subject's eye (E) is captured along the imaging axis 110. In an aspect, the illumination light beam and a photographic light beam may be transmitted in the direction shown by arrow A in the FIG. 1a, and the reflections from eye E are transmitted in the direction towards the imaging module as shown by arrow B in the FIG. 1a.

In an embodiment, during the photographic mode of the imaging apparatus 100, the observation light source 120 may be switched ON. In another embodiment, during the photographic mode of the imaging apparatus 100, the observation light source 120 may be switched OFF. The first shield 125 serves to prevent corneal reflections during the photographic mode. For instance, the first shield 125 blocks central portion of a photographic light beam and thereby prevents the corneal reflections. Thus, the reflex-free image of the retina or the fundus is obtained. The image of the retina that is received by the imaging module 181, for example, a smart phone, can be processed, stored, or transmitted to remote servers or computers for storage and evaluation.

Thus, with the help of at least the first shield 125, the second shield, 130, the porosity mirror 165, and the porosity tube 170, the corneal reflections are prevented during the live view mode and the photographic mode of the imaging apparatus 100. Further, the observation light source 120 and the photographic light source 115 are arranged on same optic axis, i.e., the illumination axis 105. Thus, the imaging apparatus 100 of the present subject matter is compact and requires less space.

The lens and other components described herein may be made of a suitable material such as a precisely machined glass. Alternatively, transparent plastic materials may be used for the purpose provided the refractive index and other optical properties match the requirements of the retinal imaging device. Methods of making precisely machined glass to provide lens to be used in the retinal imaging device are well known in the art. Further, the relative positioning of each lens with respect to each other lenses is well known in the art and may be arrived at without undue experimentation by one skilled in the art.

FIG. 2 shows an arrangement of LEDs on the first shield 125 of the FIG. 1b, in accordance with an embodiment of the present subject matter. As mentioned previously, the observation light source 120 comprises plurality of LEDs 205.

In an embodiment, the plurality of LEDs 205 are arranged on the central opaque portion 182 of the first shield 125, as shown in the FIG. 2, and each LED of the plurality of LEDs 205 operate at a predefined wavelength of light. For example, the plurality of LEDs 205 are arranged in one or more rings on the central opaque portion 182 of the first shield 125, and LEDs in each ring operates at a predefined wavelength of light. For the sake of brevity, only five LEDs are shown in the FIG. 2. However, it is understood to a person skilled in the art that any number of LEDs can be used. In an embodiment, the plurality of LEDs 205 is mounted at center on the central opaque portion 182 of the first shield 125 along the illumination axis 105. In another embodiment, the observation light source 120 is mounted between the center and periphery of the central opaque portion 182 of the first shield 125. For instance, the observation light source 120 is mounted very close to the center of the central opaque portion 182 of the first shield 125. Thus, the present subject matter reduces loss of light by mounting the plurality of LEDs 205 either at the center or between the center and periphery of the central opaque portion 182 of the first shield 125, rather than mounting the observation light source 120 around the circumference of the first shield 125 as disclosed in conventional arts.

Further, one or more LEDs of the plurality of LEDs 205 are selected in such a way that the imaging apparatus 100 can be operated in one of a mydriatic mode, a non-mydriatic mode, red free FFA, ICG, etc. In an embodiment, one or more of the plurality of LEDs 205 are infrared LEDs, and the infrared LEDs are switched ON to operate the imaging apparatus 100 in a non-mydriatic mode. The infrared LEDs operate at a wavelength of light greater than 700 nm, for example, 800 nm. The infrared LEDs can be used for observing the subject's eye E. In another embodiment, one or more of the plurality of LEDs 205 are white LEDs, and the white LEDs are switched ON to operate the imaging apparatus 100 in a mydriatic mode. The white LEDs can be used for at least one of fundus observation and photographing.

In an embodiment, for operating the imaging apparatus 100 in a non-mydriatic mode, one or more LEDs, which are infrared LEDs, are selected from the plurality of LEDs by operating the control circuit 190, which is adapted to control the operation of the plurality of LEDs. In another embodiment, for operating the imaging apparatus 100 in the mydriatic mode, one or more LED's, which are white LEDs, are selected from the plurality of LEDs 100 by operating the control circuit 190.

Figure 3:
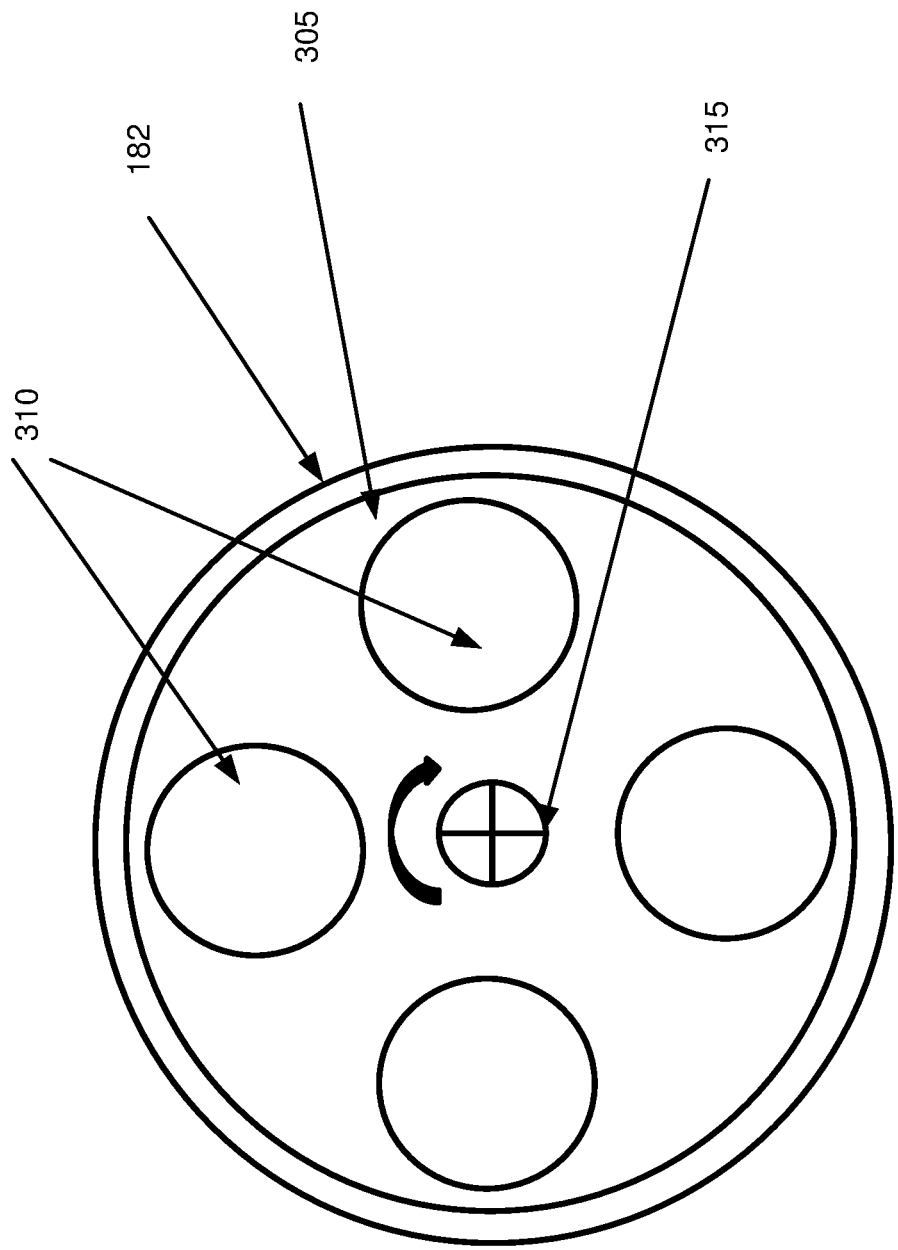
FIG. 3 shows a rotatable turret assembly mounted on the first shield of the FIG. 1a, in accordance with an embodiment of the present subject matter.

FIG. 3 shows a rotatable turret assembly mounted on the first shield 125 of the FIG. 1b, in accordance with an embodiment of the present subject matter. As mentioned previously, the observation light source 120 comprises plurality of LEDs 310, which can operate at different predefined wavelengths of light. In an embodiment, the observation light source 120 comprises the rotatable turret assembly 305 mounted with the plurality of LEDs 310 of one or more predefined wavelengths of light. For example, the observation light source 120 is mounted on the central opaque portion 182 of the first shield 125. In an embodiment, the observation light source 120 is mounted at center on the central opaque portion 182 of the first shield 125 along the illumination axis 105. In another embodiment, the observation light source 120 is mounted between the center and periphery of the central opaque portion 182 of the first shield 125. For instance, the observation light source 120 is mounted very close to the center of the central opaque portion 182 of the first shield 125. Thus, the present subject matter reduces loss of light by mounting the observation light source 120 either at the center or between the center and periphery of the central opaque portion 182 of the first shield 125, rather than mounting the observation light source 120 around the circumference of the first shield 125 as disclosed in conventional arts.

Further, a rotational axis 315 of the rotatable turret assembly 305 is parallel to the illumination axis 110 and separated from the illumination axis 105 is such a way so that the center of each of the LEDs is aligned on the illumination axis 105 when the rotatable turret assembly 305 is rotated to select one or more LEDs of the plurality of LEDs 310 operating a specific wavelength.

In an embodiment, the rotatable turret assembly 305 may be rotated to select infrared LEDs of the plurality of LEDs 310 to operate the imaging apparatus 100 in a non-mydriatic mode. In another embodiment, the rotatable turret assembly 305 may be rotated to select white LEDs of the plurality of LEDs 310 to operate the imaging apparatus 100 in a mydriatic mode. Thus, the present subject matter prevents the corneal reflections and reduces the loss of light.

Although embodiments for ophthalmologic imaging apparatus which can produce reflex-free retinal images have been described in language specific to structural features and/or methods, it is to be understood that the appended claims are not necessarily limited to the specific features or the methods described. Rather, the specific features and methods are disclosed as example embodiments.

We claim:

1. An ophthalmologic imaging apparatus to capture retinal images of a subject's eye, the ophthalmologic imaging apparatus comprising:
    a photographic light source arranged on an illumination axis;
    a first condenser lens placed in front of the photographic light source on the illumination axis;
    a first shield placed in front of and at a distance from the first condenser lens, wherein the first shield has a central opaque portion and an outer pair of coaxial annular transparent regions;
    an observation light source mounted on the central opaque portion of the first shield in front of the first shield, wherein the observation light source is arranged on the illumination axis;
    a diffuser placed in front of the observation light source to diffuse an illumination light beam emitted from the observation light source;
    a second shield mounted in front of and on the diffuser to receive diffused light from the diffuser, wherein the second shield has a central opening portion bounded by a first opaque ring, an outer pair of coaxial annular opaque portions forming a second opaque ring, and a donut shaped open portion formed between the first opaque ring and the second opaque ring, and wherein the second shield creates an annular illumination pattern from the illumination light beam that passes through the donut shaped open portion;
    a porosity tube disposed in front of and at a distance from the second shield, wherein the porosity tube is axially aligned along an imaging axis that is perpendicular to the illumination axis;
    a porosity mirror mounted on the porosity tube, wherein the porosity mirror is at an angle with respect to the imaging axis; and
    an imaging module aligned along the imaging axis and perpendicular to the illumination axis, wherein the imaging module captures the retinal images of the subject's eye.

2. The ophthalmologic imaging apparatus as claimed in claim 1, wherein the observation light source comprises a halogen lamp.

3. The ophthalmologic imaging apparatus as claimed in claim 1, wherein the first shield and the second shield are ring shaped.

4. The ophthalmologic imaging apparatus as claimed in claim 1, wherein the observation light source is mounted at center on the central opaque portion of the first shield along the illumination axis.

5. The ophthalmologic imaging apparatus as claimed in claim 1, wherein the observation light source is mounted between center and periphery of the central opaque portion of the first shield along the illumination axis.

6. The ophthalmologic imaging apparatus as claimed in claim 1, wherein the ophthalmologic imaging apparatus comprises a transparent plate having a black dot absorber and the transparent plate is placed between the second shield and the porosity tube.

7. The ophthalmologic imaging apparatus as claimed in claim 6, wherein the ophthalmologic imaging apparatus comprises a second condenser lens placed between the transparent plate- and the second shield.

8. The ophthalmologic imaging apparatus as claimed in claim 6, wherein the ophthalmologic imaging apparatus comprises at least one projection lens placed between the porosity tube and the transparent plate.

9. The ophthalmologic imaging apparatus as claimed in claim 1, wherein the observation light source comprises plurality of LEDs, and the ophthalmologic imaging apparatus comprises a control circuit control the operation of the plurality of LEDs.

10. The ophthalmologic imaging apparatus as claimed in claim 9, wherein the observation light source comprises a rotatable turret assembly mounted with the plurality of LED's of one or more predefined wavelengths, and a rotational axis of the rotatable turret assembly is parallel to the illumination axis and separated from the illumination axis is such a way so that the center of each of the LEDs is aligned on the illumination axis when the rotatable turret assembly is rotated to select one or more LEDs of the plurality of LEDs operating a specific wavelength.

11. The ophthalmologic imaging apparatus as claimed in claim 9, wherein the plurality of LEDs are arranged on the central opaque portion of the first shield, and each LED of the plurality of LEDs operate at a predefined wavelength of light.

12. The ophthalmologic imaging apparatus as claimed in claim 11 wherein one or more of the plurality of LEDs are white LEDs to operate the ophthalmologic imaging apparatus in a mydriatic mode.

13. The ophthalmologic imaging apparatus as claimed in claim 11, wherein one or more of the plurality of LEDs are infrared LEDs to operate the ophthalmologic imaging apparatus in a non-mydriatic mode.

14. The ophthalmologic imaging apparatus as claimed in claim 13, wherein the infrared LEDs operate at a wavelength of light greater than 700 nm.

* * * * *